United States Patent [19]

Wu et al.

[11] Patent Number: 5,466,868
[45] Date of Patent: Nov. 14, 1995

[54] PROCESS FOR THE PREPARATION OF AN ENRICHED 2,2'-OXYDISUCCINATE REACTION MIXTURE BY REMOVAL OF CALCIUM MALATE

[75] Inventors: Shang-Ren Wu, Mahwah; Donna Wu, North Bergen; Eddie N. Gutierrez, Midland Park, all of N.J.

[73] Assignee: Lever Brothers Company, Division of Conopco, Inc., New York, N.Y.

[21] Appl. No.: 323,301

[22] Filed: Oct. 14, 1994

[51] Int. Cl.$^6$ .......................... C07C 51/42; C07C 51/43
[52] U.S. Cl. ............................. 562/580; 562/583
[58] Field of Search ...................... 562/580, 583

[56] References Cited

U.S. PATENT DOCUMENTS

| | | | |
|---|---|---|---|
| 3,128,287 | 4/1964 | Berg | 260/346.8 |
| 3,635,830 | 1/1972 | Lamberti et al. | 252/152 |
| 3,914,297 | 10/1975 | Lamberti et al. | 260/535 P |
| 4,798,907 | 1/1989 | MacBrair, Jr. et al. | 562/583 |
| 4,959,496 | 9/1990 | Crutchfield et al. | 562/583 |
| 5,030,751 | 7/1991 | Lamberti et al. | 562/583 |
| 5,068,420 | 11/1991 | Kreczmer | 562/583 |
| 5,104,568 | 4/1992 | Shaw, Jr. et al. | 252/174.18 |
| 5,254,281 | 10/1993 | Pichardo et al. | 252/108 |
| 5,296,588 | 3/1994 | Au et al. | 536/1.11 |
| 5,336,765 | 8/1994 | Au et al. | 536/18.5 |

FOREIGN PATENT DOCUMENTS 2030985  6/1991  Canada.

OTHER PUBLICATIONS

Abstract of JP 4112849 (1992).
Abstract of JP 4112850 (1992).
Defensive Publication No. T101,805—published May 4, 1982, Lamberti.

Primary Examiner—Joseé G. Dees
Assistant Examiner—Barbara S. Frazier
Attorney, Agent, or Firm—James J. Farrell

[57] ABSTRACT

A process for the preparation of enriched reaction mixtures containing 2,2'-oxydisuccinate (alkaline earth metal salts) is disclosed, by pH reduction and removal of alkaline earth metal malates.

10 Claims, No Drawings

PROCESS FOR THE PREPARATION OF AN ENRICHED 2,2'-OXYDISUCCINATE REACTION MIXTURE BY REMOVAL OF CALCIUM MALATE

BACKGROUND OF THE INVENTION

1. Field of the Invention

The invention relates to the preparation of enriched reaction mixtures containing the alkaline earth metal salts of 2,2'-oxydisuccinic acid by a process which removes the salt of alkaline earth metal malates.

2. Related Art 2,2'-oxydisuccinic acid (ODS) and salts thereof are useful as sequestering agents and detergent builders. A disadvantage of ODS and its salts as detergent builders is that they may be relatively expensive to prepare.

U.S. Pat. No. 3,128,287 to Berg discloses a preparation of ODS salt by admixing maleic acid with an excess of hydroxide of calcium, barium, magnesium or strontium in the presence of water, then heating the reaction mixture from about one day to about one month at temperatures ranging from 50° C. to reflux temperatures. The process yields a mixture of malic acid and ODS. Berg's Example I teaches the preparation of ODS, wherein the aqueous mixture of maleic anhydride and calcium hydroxide is reacted at reflux (100° C.) for 4 days. Subsequently, ODS salt is isolated from the product containing ODS and malic acid salts.

U.S. Pat. No. 3,635,830 to Lamberti et al., discloses a process for the preparation of ODS based on the process of Berg. The patent teaches separation/purification of two diastereoisomeric forms of ODS obtained by the Berg process. The patent also discloses detergent compositions comprising ODS or salts thereof as detergent builders.

U.S. Pat. No. 5,030,751 to Lamberti discloses methods of preparing mixed salts of ODS and carboxymethyloxysuccinic acid.

U.S. Pat. No. 4,959,496 to Crutchfield discloses a process for preparing ether carboxylates and precipitating and recycling unreacted starting materials by reducing the pH to 4.5 to 5.5.

Japanese patents JP 4112849 and JP 4112850 disclose preparation of metallic salts of ether carboxylates by the addition of maleic acid or maleic anhydride to an aqueous mixture of an alkali metal salt of a hydroxycarboxylic acid and alkaline earth metal carbonate.

A workable and cost-efficient production of ODS salt must be directed towards optimizing the process conditions in ways which improve yields of the ultimate product without increasing expense. There have been different approaches to the problem of producing ODS at a lower cost. However, none of these approaches has been completely satisfactory.

Accordingly, it is an object of the present invention to provide a process which ultimately produces the alkaline earth metal salts of ODS in high yields by enriching the ODS content of the reaction mixture.

This and other objects and advantages will appear as the description proceeds.

SUMMARY OF THE INVENTION:

The attainment of the above objects is made possible by this invention which includes preparation of the alkaline earth metal salts of ODS by a process which enriches the ODS content of a reaction mixture comprising the steps of:

(i) preparing an aqueous reaction mixture having a substantial absence of alkali metal and containing primarily alkaline earth metal salts of ODS in solution;

(ii) reducing the pH of the reaction mixture to about 8.8 with an appropriate acidifying agent;

(iii) allowing the reaction mixture to stand for at least about 10 hours to permit formation and precipitation of alkaline earth metal malate salts;

(iv) removal of the precipitate to form the enriched ODS reaction mixture;

(v) subsequent recovery of the ODS salts.

The reaction mixture containing the alkaline earth metal ODS may be prepared by known methods provided that there is an excess of alkaline earth metal, preferably calcium and a substantial lack of alkali metal, for example, sodium. The methods disclosed in copending patent application Ser. No. 08/198,401 and incorporated herein by reference are appropriate where the preparation includes the steps of:

(i) dissolving
   (a) Maleic anhydride, maleic acid or mixtures of these; and
   (b) Malic acid including R, S and mixtures of R and S; in
   (c) Water, in a ratio of 1.2 to 5.0 moles of maleic species to 1.0 moles of malic species to form an acid solution or mixture containing some undissolved solids;

(ii) mixing the acid solution or mixture with a slurry of alkaline earth metal hydroxide, to form a reaction mixture, the slurry containing a stoichiometric amount of the alkaline earth metal hydroxide, preferably $Ca(OH)_2$, to neutralize said acid, plus about 10% in excess of this amount, but in any case sufficient to maintain the pH of the mixture at about 11.0 to 12.3 when measured at 25° C. and 20% solids. The slurry contains sufficient water so that the reaction mixture of acid solution and slurry contains at least about 40% by weight water. Preferably the acid solution or mixture is added to the hydroxide slurry. The acid solution has solid loadings of about 36% or higher. Additional solid acid and hydroxide, if necessary, are preferably added to the reaction mixture;

(iii) after forming the reaction mixture, maintaining its temperature at about 60° C. to 95° C. for about 2 to 8 hours, optionally employing an atmosphere inert to the reactants, such as nitrogen and the like.

Instead of solutions of malate and maleate, solid powdered or comminuted species may also be employed as disclosed in companion case UNUS Docket No. 93-R001-EDG. By the use of solid materials, solid loadings of up to 60% may be achieved.

In general, the process of preparation involves running the reaction at a sufficient temperature for a sufficient time to form the final product while maintaining the following parameters:

A. Insuring solubility of the final ODS and other components in concentrations from about 5% up to about 45% to 60% by weight of solute by varying the temperature of reaction between about 60° C. where this higher amount of ODS and other components is substantially completely soluble up to about 95° C. where ODS and other components are only marginally soluble. Optionally, the reaction can be continued at temperatures lower than 60° C. to obtain higher yields, without encountering substantial phase separation.

B. Insuring that the solubility of the ODS and other components is never substantially exceeded at a particular temperature. This is accomplished by varying the time at which the reaction is held at that temperature to guarantee that the total concentration of ODS and other components do not substantially exceed their solubility limitations at the temperature in question. If phase separation occurs it is reversible but time consuming. The solubility of the calcium salt is important to avoid phase separation, keeping in mind the inverse nature of the calcium salt solubility, i.e., the salt is more soluble at cooler temperatures within the range. It should be noted that at low concentrations of solids, for example, concentrations of 20% then ratios of maleic to malic of less than 1.2 to 1 are sometimes employed to advantage.

Control of the molar ratio of the alkaline earth metal hydroxide to organic reactants, the ratio of maleate to malate, the amount of water in the reaction mixture and the reaction temperature of about 60° to 95° C. are critical to obtain the ODS salt product in about 5 hours and to avoid substantial phase separation of the reaction mixture.

In its broadest aspect, the invention provides a process for eliminating alkaline earth metal salts of malic acid to permit recovering an alkaline earth metal, preferably calcium, salt of ODS which may then be more easily isolated from other organic species contained in the reaction mixture because of enrichment. The ODS salt can be obtained by the inventive process and converted to ODS acid (Formula I below).

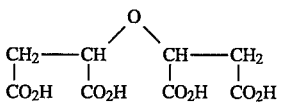

FORMULA I or ODS salts such as monovalent cation salts, ammonium salts, morpholinium salts, alkanol ammonium salts and mixtures thereof, by methods known in the art. Such methods are disclosed, for example, in U.S. Pat. No. 3,128,287 to Berg and U.S. Pat. No. 3,635,830 to Lamberti et al. discussed above and incorporated herein by reference. As noted, the 3,635,830 patent also discloses detergent compositions containing ODS or salts thereof.

In defining the purification and enrichment process of this invention, it is intended to include both batch and continuous processes.

DETAILED DESCRIPTION OF THE INVENTION

The process of this invention for enriching the reaction mixture with the alkaline earth metal salts of ODS while minimizing byproducts is outlined as follows:

(i) preparing an aqueous reaction mixture having a substantial absence of alkali metal and containing primarily alkaline earth metal salts of ODS in solution;

(ii) reducing the pH of the reaction mixture to about 8.7 to 8.9 with an appropriate acidifying agent;

(iii) allowing the reaction mixture to stand for at least about 10 hours and diluting if desired, to permit formation and precipitation of alkaline earth metal malate salts;

(iv) removal or separation of the precipitate to form the enriched ODS salt reaction mixture;

(v) subsequent recovery of the ODS salt.

The reaction mix can have the pH reduced by any convenient method such as addition of hydrochloric acid, sulfuric acid, malic acid or ion exchange resins, for example, amberlite 1R-120. The reaction mixture is held at pH 8.7 to 8.9, preferably 8.8, at room temperature (60° F.–80° F.) for at least about 10 hours and preferably longer, up to 50 to 60 hours or more. The alkaline earth metal malate salt that forms, preferably calcium malate, takes advantage of the insolubility of alkaline earth metal malates when compared to the maleate, ODS and fumarate salts. The malate salt crystallizes out and can be removed by filtration, leaving the reaction mixture enriched in the ODS salt.

The process of this invention for enrichment of the reaction mixture containing the alkaline earth metal salt of ODS includes forming an aqueous mixture of starting reactants containing a malate moiety, a maleate moiety and an alkaline earth metal salt of ODS, preferably calcium, and a mimimum amount of alkali metal ion such as sodium. The chemically suitable forms of malate and maleate reactants include acids and the anhydride of maleic acid. The molar ratio of maleate to malate is about 5.0:1 to about 1.2:1.

The alkaline earth metal ion in the reaction mixtures of the inventive process may be selected from the group consisting of barium, strontium or calcium. The most preferred alkaline earth metal for use in this invention is calcium.

The ODS salt forming reaction is conducted at high concentration in aqueous media to afford efficacy and high throughput. The amount of water present may vary and is preferably sufficient to permit the reaction to proceed, with the amount of water being about 40% to 95%. The amount may, however, be more or less depending on design parameters.

Desirably, the reactants of the starting mixture for the process are combined in water using physical agitation. In the preferred embodiments of the invention, an alkaline earth metal hydroxide is mixed with an aqueous or solid mixture of the malate and maleate moieties producing what is believed to be a soluble mixed calcium complex. The reaction is carried out in an apparatus equipped with stirring means. The apparatus may also be equipped with a condenser to provide some means of condensing vaporized water so that it returns to the reaction mixture. The reaction is preferably conducted at atmospheric pressure.

The reaction temperature for the enrichment or purification is at room temperature, i.e. about 60° F. to 80° F. but could be slightly higher or lower. The reaction temperature is maintained for at least about 10 hours and preferably about 50 to 60 hours or even longer. The aqueous reaction product typically contains a mixture of 2,2'-oxydisuccinate, malate, maleate and fumarate salts in a concentration of about 25% to 30% by weight, but most, if not all, of the malate will precipitate as the alkaline earth metal salt. The remaining reaction mixture contains the alkaline earth metal salt of ODS in a higher proportion once the malate is removed. Of course the maleate and fumarate salts are left also but these impurities are usually minor.

The end result of the reaction products obtained by the processes of this invention contain the alkaline earth metal salt of ODS and may be worked up by methods known in the art. Generally, the work up comprises the steps of reduction of calcium content in the product mixture and acidification or conversion into monovalent cation salts, ammonium salts, morpholinium salts, alkanol ammonium salts and mixtures thereof.

The alkaline earth metal content of the ODS products may be reduced by conventional means. For example, removal of calcium can be carried out in a number of ways known in the art. In general, simply adding a calcium precipitating material will suffice. Such calcium precipitating materials include alkali metal carbonate, pyrophosphate, sulfates, bicarbonate and/or alkali metal silicate and mixtures thereof, for example, the addition of sodium carbonate will convert the alkaline earth metal salt obtained to the sodium salt. The resulting calcium precipitate can thereafter be removed from the aqueous reaction product mixture by filtration. In an alternative mode, removing calcium from the aqueous reaction product mixtures involves treatment of said mixtures with an appropriate insoluble ion exchange resin or zeolite. No matter what technique is employed, the calcium content of the ODS salt prepared by methods herein should desirably be reduced to the extent that calcium is present in an amount of no more than about 1.0% of the ODS salt and preferably less than 0.2%, in order to form compositions particularly suitable as detergent builders. This can be accomplished by the method of defensive publication T 101,805.

ODS salts recovered can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired ODS salt is relatively insoluble as disclosed in U.S. Pat. No. 5,068,420.

At any stage after the ODS salt recovery, and after reducing the calcium salt content the reaction product can be concentrated by removal of water to the desired extent. Water removal can, for example, after calcium removal, involve substantially complete drying of the reaction product mixture, e.g., by spray drying, so that the ODS salt is recovered in solid, e.g., granular, form. The sodium salt of ODS in the form of aqueous liquid may be utilized directly in the preparation of detergent compositions or laundry additive products of the types more fully described hereinafter.

It is also possible, if desired, to acidify the product mixtures using conventional acidification or ion exchange techniques to convert the ODS salts to their free acid form. Normally, however, the ODS materials of this invention can, after calcium depletion or complete replacement by sodium, be used as builders in their water-soluble salt form, and such acidification is therefore not usually necessary or desirable.

When converted into suitable form, the ODS salts can be used as sequestering builders in a wise variety of detergent or laundry additive compositions.

Detergent compositions incorporating the ODS salt prepared using the processes of this invention contain as essential components from about 0.5% to about 98% of a surfactant and from about 2% to about 99.5% of the ODS compounds as a detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The ODS builder can be used either as the sole builder or where desired can be used in conjunction with other well-known builders, examples of which include water-soluble salts of phosphates, pyrophosphates, ortho-phosphates, polyphosphates, phosphonates, carbonates, polyhydroxysulfonates, polyacetates, carboxylates, polycarboxylates, succinates and the like.

In addition to the surfactant and builder there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from about 9 to about 11.

In addition to their utility as builders in detergent and laundry additive compositions, the ODS salts of the invention can, after reducing their calcium content, also be utilized in other contexts wherein water hardness sequestration is required. Other uses are provided in water softening compositions, devices and methods and boiler descaling compositions and methods. It is also theorized that ODS can complex heavy metals which react with bleach and thus can stabilize bleach.

It should also be noted that when ODS is employed as the free acid or as partly neutralized salt it has utility in metal cleaning composition under pH conditions of about 2 to about 5. The following examples are designed to illustrate, but not to limit, the practice of the instant invention. All percentages and parts herein are by weight unless indicated otherwise. All ratios herein are mole ratios unless indicated otherwise. R, S- malic acid is used in the Examples unless indicated otherwise.

Reaction mixture samples and reaction products were analyzed by HPLC and/or NMR. The HPLC analysis is carried out using a Hitachi instrument. The mobile phase is a 30/70 acetonitrile/water mixture with 0.75 g/l of 85% phosphoric acid at a pH of about 3 to 4. The column is an RP/SAX Regis 25 cm×4.6 mm in dimension. The flow rate is 1.5 ml/minute. The wavelength at which the detector is set is 210 nm. Samples are diluted with the mobile phase. Quantification is done using an external standard. The volume of the injections used are 50 µl.

The NMR is a 200 MHz Bruker model. Samples are prepared by ion exchanging the calcium salts, followed by neutralization of the acids with sodium carbonate, drying, and dissolution in $D_2O$. Peak assignments are as follows:

Fumaric 6.28δ

Maleic 5.78δ

Malic CH 4.1 to 4.3δ$CH_2$ 2.0 to 2.5δ (overlap with ODS)

ODS CH 3.83 to 3.59δ$CH_2$ 2.0 to 2.5δ (overlap with malic)

EXAMPLE 1

A solid mixture of 22.5 g (0.23 mole) of maleic anhydride and 25 g (0.19 mole) of malic acid is added gradually to a slurry of 33.3 g (0.45 mole) of calcium hydroxide in 120 ml of water, while the temperature is maintained at 50° C. The slightly hazy solution is held at 65°–70° C. for three hours to form the calcium salts of ODS. To the solution is added 110 ml water, followed by the slow addition of 3.2 g of malic acid down to a pH of 8.7–8.8 The mixture is allowed to remain at R.T. for 50–60 hours and the crystals that are produced are dried at 125° C. overnight. Twelve grams of calcium malate, NMR confirmed, are recovered. The concentration of salts in the reaction mixture before and after malic treatment are listed below (in wt. %):

|  | ODS | MALIC | MALEIC | FUMARIC |
|---|---|---|---|---|
| Before | 69.5 | 14.2 | 15.2 | 1.0 |
| After | 81.9 | 0.5 | 16.2 | 1.4 |

It is understood that the examples and embodiments described herein are for illustrative purposes only and that various modification or changes in the light thereof will be suggested to persons skilled in the art and are to be included within the spirit and purview of this application and the scope of the appended claims.

What is claimed is:

1. A process for preparing the alkaline earth metal salts of 2,2'-oxydisuccinic acid in high purity comprising:
   (i) preparing a reaction mixture of said alkaline earth metal salt combined with malate, maleate and fumarate salts in the substantial absence of any alkali metal ion or salts;
   (ii) adding sufficient acidifying agent to said reaction mixture to achieve a pH of about 8.7 to 8.9 to form a slurry;
   (iii) precipitating the alkaline earth metal salt of malic acid from the slurry;
   (iv) separating the alkaline earth metal salt of malic acid from the slurry to form an enriched mixture of 2,2'oxydisuccinic alkaline earth metal salt in the slurry.

2. A process as defined in claim 1 wherein the reaction is extended for a period of about 10 to 100 hours at ambient temperature.

3. A process as defined in claim 1 wherein the alkaline earth metal is calcium.

4. A process as defined in claim 1 wherein the pH is 8.8.

5. A process as defined in claim 1 wherein the slurry is filtered to remove the alkaline earth metal salt of malic acid.

6. A process as defined in claim 1 wherein the concentration of maleic and malic species as the calcium salt at the beginning of the reaction is about 5% to 60%.

7. A process as defined in claim 1 wherein the concentration of maleic and malic species as the calcium salt at the beginning of the reaction is about 40% to 50%.

8. A process as defined in claim 1 wherein the alkali metal content is less than about 0.001 mole.

9. A process as defined in claim 1 having less than about 0.001 mole of sodium.

10. A process as defined in claim 1 wherein said acidifying agent is selected from the group consisting of malic acid, sulfuric acid, hydrochloric acid, ion exchange resin and mixtures thereof.

* * * * *